United States Patent

Ainsworth et al.

[11] 4,329,358
[45] May 11, 1982

[54] 3-CHLOROPHENYL ANTI-OBESITY AGENTS

[75] Inventors: Anthony T. Ainsworth, Cranleigh; David G. Smith, Redhill, both of England

[73] Assignee: Beecham Group Limited, England

[21] Appl. No.: 200,430

[22] Filed: Oct. 24, 1980

[30] Foreign Application Priority Data

Oct. 25, 1979 [GB] United Kingdom ............... 7937084

[51] Int. Cl.$^3$ ................ A61K 31/24; C07C 101/42
[52] U.S. Cl. ................................ 424/309; 424/319; 424/324; 560/42; 562/451; 564/165
[58] Field of Search ............... 560/42; 562/451; 564/165; 424/309, 319, 324

[56] References Cited

U.S. PATENT DOCUMENTS 3,723,524 3/1973 Augstein et al. ............... 564/165
3,911,008 10/1975 Edinberry et al. ............. 564/165
4,086,272 4/1978 Cox et al. ..................... 564/165
4,140,713 2/1979 Oxford et al. .

FOREIGN PATENT DOCUMENTS 6735 1/1980 European Pat. Off. .
6766 1/1980 European Pat. Off. .

Primary Examiner—G. T. Breitenstein
Attorney, Agent, or Firm—Jacobs & Jacobs

[57] ABSTRACT

Compounds of formula (III):

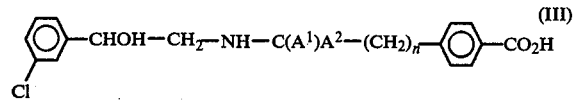

and esters, amides and pharmaceutically acceptable salts thereof, wherein
$A^1$ is hydrogen or methyl;
$A^2$ is hydrogen or methyl; and
n is 1, 2 or 3
have anti-obesity activity. Methods for their preparation pharmaceutical formulations of the compounds and their use in medicine are described.

10 Claims, No Drawings

3-CHLOROPHENYL ANTI-OBESITY AGENTS

The present invention relates to a group of secondary amine derivatives that possess anti-obesity and anti-hyperglycaemic properties, to the method of their preparation and to their use as anti-obesity and/or anti-hyperglycaemic agents when formulated into a pharmaceutical composition.

Certain of the compounds within the formula (I):

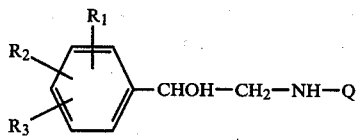

wherein $R_1$ is a hydrogen, fluorine or chlorine atom or a hydroxyl, hydroxymethyl, methyl, methoxyl, amino, formamido, acetamido, methylsulphonylamido, nitro, benzyloxy, methylsulphonylmethyl, ureido, trifluoromethyl or p-methoxybenzylamino group; $R_2$ is a hydrogen, fluorine or chlorine atom or a hydroxyl group; $R_3$ is a hydrogen or chlorine atom or a hydroxyl group; and Q is an isopropyl or t-butyl group; are known to possess β-adrenoceptor agonist activity (see for example D. T. Collins et al., J. Med. Chem., 1970, 13, 674). Certain compounds within formula (I) wherein Q is a group such as a phenylaminoethyl were disclosed in Belgian Pat. No. 851232 as possessing β-adrenoceptor stimulant activity. Belgian Pat. No. 809831 disclosed that certain compounds within formula (I) wherein Q is inter alia a substituted phenylethyl group are useful as medicaments for the treatment of skin diseases. U.S. Pat. No. 3,818,101 disclosed certain compounds within formula (I) wherein Q could be inter alia an aralkyl group which may be used to induce polyphagia in meat producing animals. Certain compounds within the formula (I) wherein Q may be hydroxybenzyl or alkoxybenzyl group were indicated as possessing β-adrenergic stimulant and blocking properties in South African Pat. No. 67/5591. The preceding publications do not describe compounds of the formula (I) as possessing anti-obesity activity coupled with anti-hyperglycaemic activity nor indeed do they describe compounds of the formula (I) as possessing anti-obesity activity alone. We have discovered a group of compounds somewhat related to those of the formula (I) which possess anti-obesity properties and/or anti-hyperglycaemic properties. Such compounds may thus be used in the treatment of obesity or hyperglycaemia and can be envisaged as being of particular interest in conditions such as maturity onset diabetes where obesity is often linked with hyperglycaemia. European Patent Application No. 79301197.4 provided the compounds of the formula (II):

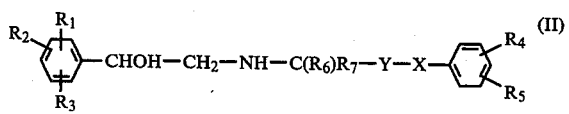

or a pharmaceutically acceptable salt thereof wherein $R_1$ $R_2$ and $R_3$ are as defined in relation to formula (I); $R_4$ is a carboxylic acid group or a salt, ester or amide thereof; $R_5$ is a hydrogen, chlorine or fluorine atom or a methyl, methoxyl or hydroxyl group or a carboxylic acid group or a salt, ester or amide thereof; $R_6$ is a hydrogen atom or a methyl, ethyl or propyl group; $R_7$ is a hydrogen atom or a methyl, ethyl or propyl group; X is an oxygen atom or a bond; and Y is an alkylene group of up to 6 carbon atoms or a bond. Such compounds were shown to have desirable anti-obesity and anti-hyperglycaemic activity.

It has now been discovered that a small group of compounds within formula (II) have particularly good anti-obesity and anti-glycaemic properties coupled with a particularly low level of side-effects.

The present invention provides the compounds of the formula (III):

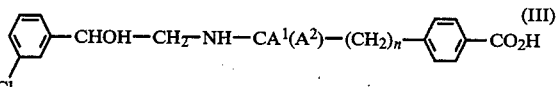

and esters, amides and pharmaceutically acceptable salts thereof wherein $A^1$ is a hydrogen atom or a methyl group and $A^2$ is a hydrogen atom or a methyl group and n is 1,2 or 3.

Preferably $A^1$ is a methyl group. Preferably $A^2$ is a hydrogen atom. Preferably n is 1 or 2.

Suitably, $A^1$ and $A^2$ are each hydrogen atoms, and n is 1 or 2.

The esters of the compounds of the formulae (III) and (IV) may be any set forth as suitable in the aforementioned European Application which, together with U.S. Ser. No. 051,440, incorporated herein by reference.

Particularly apt esters of the compounds of the formulae (III) and (IV) include $C_{1-4}$ alkyl esters such as the methyl, ethyl, isopropyl and n-propyl esters.

A preferred ester of the compounds of the formulae (III) and (IV) is the methyl ester.

The amides of compounds of formulae (III) and (IV) may be any of those set forth in the aforementioned European and U.S. Patent Applications and thus include unsubstituted, mono- and di-($C_{1-4}$) alkyl substituted amides and amides having a 5, 6 or 7 membered cyclic amino moiety.

Preferred amides include unsubstituted amides and mono-($C_{1-4}$) alkyl substituted amides, the unsubstituted amide and methyl substituted amide being particularly preferred.

Esters and amides of the compounds of the formulae (III) and (IV) may be provided in the form of an acid addition salt with a pharmaceutically acceptable acid and the compounds of formula (III) may also be provided as such acid addition salts. Suitable acid addition salts include those formed with acids such as hydrochloric, hydrobromic, orthophosphoric, sulphuric, methanesulphonic, toluenesulphonic, acetic, propionic, lactic, citric, fumaric, malic, succinic, salicylic, acetylsalicylic or the like acid.

The compounds of the formula (III) have a centre of asymmetry at the carbon atom marked with a single asterisk in formula (IIIa):

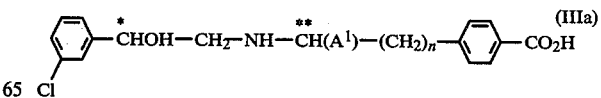

wherein $A^1$ and n are as defined in relation to formula (III). The compounds of the formula (III) have another centre of asymmetry at the carbon atom marked with two asterisks in formula (IIIa) when $A^1$ is a methyl group.

The present invention extends to the individual stereoisomeric forms of the compounds of the formula (III) as well as to mixtures thereof. Aptly those compounds of the formula (III) which contain two asymmetric centres are provided in the form of the separated diastereoisomers. Such separated diastereoisomers will, of course, contain a pair of compounds which are mirror images of each other.

Preferred stereoisomers are those with the R absolute stereochemistry at the C* centre of asymmetry.

X-Ray analysis may be used to determine and correlate absolute stereochemistry.

It is believed that in the $^{13}C$ n.m.r. of compounds of formula (III) containing a methyl group on the carbon atom $\alpha$ to the nitrogen atom, the more active diastereomer is that in which said methyl group appears at higher field (the lower numerical value when expressed in ppm) in $d_6DMSO$ solution. The paired resonances often appear at approximately 20 ppm (less active) and slightly below 20 ppm (more active) down field from tetramethylsilane. Other paired resonances can occur for the carbon atoms attached directly to the nitrogen atom and the carbon $\beta$ to nitrogen which carries the hydroxyl group. Again the more active diasteromer of the investigated compounds has the higher field position of the paired resonances.

The present invention also provides a pharmaceutical composition which comprises a compound of this invention and a pharmaceutically acceptable carrier.

The compositions of this invention will normally be formulated for oral administration although composition formulated for non-oral modes of administration, for example injection, are also envisaged.

Particularly suitable oral dosage forms are unit dose forms such as tablets or capsules. Other fixed unit dose forms such as powders presented in sachets may also be used.

In accordance with convention pharmaceutical practice the carrier may comprise a diluent, binder, filler, disintegrant, wetting agent, lubricant, colourant, flavourant or the like.

Typical carriers may, therefore, comprise such agents as microcrystalline cellulose, starch, sodium starch, glycollate, polyvinylpyrrolidone, polyvinylpolypyrrolidone, magnesium stearate, sodium lauryl sulphate, sucrose and the like.

Most suitably the composition will be provided in unit dose form. Such unit doses will normally comprise 0.1 to 500 mg, more usually 0.2 to 100 mg and favourably 0.5 to 50 mg. Such doses may be taken one to six times a day in a manner such that the total daily dose for a 70 kg adult will generally be about 0.1 to 500 mg and more usually about 1 to 100 mg.

In addition to use in human medicine the compositions of this invention may be used to treat obesity in domestic mammals, such as dogs. In general administration to domestic mammals will be by mouth and will usually take place one or two times a day at about 0.05 mg/kg to 25 mg/kg, for example 0.1 mg/kg to 5 mg/kg.

The compounds of this invention may be prepared by the processes of the aforementioned incorporated European and U.S. Patent Applications.

The present invention provides a process for the preparation of a compound of formula (III) which comprises the reduction of a compound of the formula (IV):

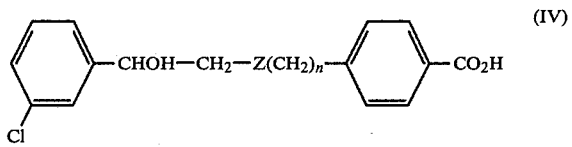

or a salt, ester or amide thereof wherein Z is a $-N=CA^1$ or $-NH-C(OH)A^1-$ group and $A^1$ and n are as defined in relation to formula (III) and thereafter if desired forming an ester, amide or addition salt of the initially produced compound of the formula (III):

The reduction of the compound of the formula (IV) may be normally effected by catalytic hydrogenation. Suitable catalysts include noble metal catalysts such as platinum, for example platinum oxide. If platinum is used as catalyst an atmospheric pressure of hydrogen may be employed. The reaction may be carried out at any convenient non-extreme temperature but it is generally most suitable to use a slightly super ambient temperature such as 30° C. to 100° C., for example 40° C. to 80° C. The hydrogenation may be carried out in a conventional hydrogenation solvent such as a lower alkanol, for example ethanol.

The desired compound may be isolated from the reaction mixture by evaporation of the filtered solution. The initially obtained product may be purified by conventional means, for example by chromatography, crystallisation or the like.

The reduction of the compound of the formula (IV) may also be effected using a complex hydride such as sodium borohydride.

This reduction is generally carried out in a lower alkanolic solvent, for example methanol if a methyl ester is desired. An approximately ambient temperature may be employed, for example 20° C. to 30° C.

The desired compound may be obtained from the reaction mixture by evaporation, extraction into a suitable solvent such as ethyl acetate and evaporation. The initially obtained product may be purified as outlined hereinbefore.

The compound of the formula (IV) may be prepared by the reaction of a compound of the formula (V):

$$\text{Cl}-\underset{}{\bigcirc}-\text{CHOH}-\text{CH}_2-\text{NH}_2 \quad (V)$$

with a compound of the formula (VI):

$$A^1-\text{CO}(CH_2)_n-\underset{}{\bigcirc}-\text{CO}_2\text{H} \quad (VI)$$

or a salt, ester or amide thereof wherein $A^1$ and n are as defined in relation to formula (III).

The preceding reaction is generally carried out under conditions that result in the removal of water formed during the reaction. Thus a convenient method is to remove the water azeotropically from a refluxing benzene solution using a Dean & Stark apparatus.

It is often convenient to prepare and utilize the compound of the formula (IV) in situ without isolation. In this case the reaction may comprise the reduction of a mixture of a compound of the formula (V) and a compound of the formula (VI) wherein $A^1$ and n are as defined in relation to formula (III).

Such a reduction may be carried out under conditions as described for the reduction of a compound of the formula (IV). The preferred method of reduction is using a complex hydride.

The compounds of the formula (III) as hereinbefore defined may also be prepared by the reaction of a compound of the formula (VII):

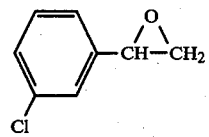
(VII)

with a compound of the formula (VIII):

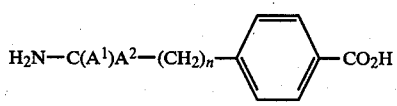
(VIII)

or a salt, ester or amide thereof wherein $A^1$, $A^2$ and n are as defined in relation to formula (III).

This reaction may be carried out in a solvent such as a lower alkanol, for example ethanol.

A further method of preparing the compounds of the formula (III) comprises the reduction of a compound of the formula (IX):

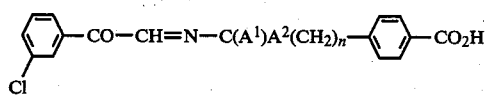
(IX)

or a salt, ester or amide thereof, wherein $A^1$, $A^2$ and n are as defined in relation to formula (III).

The reduction of the compound of the formula (IX) may be carried out using a hydride or hydrogen as described for the reduction of the compound of the formula (IV).

The compound of the formula (IX) may be prepared by the reaction of a compound of the formula (X):

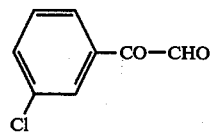
(X)

or its hydrate or hemi-acetal of a lower alkanol, with a compound of the formula (VIII):

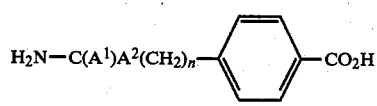
(VIII)

or a salt, ester or amide thereof, wherein $A^1$, $A^2$ and n are as defined in relation to formula (III).

The compound of the formula (IX) may be obtained from the reaction mixture by evaporation of the solvent and is normally used without purification.

Compounds of the formula (III) containing only one centre of asymmetry may be resolved in known manner, for example using an optically active acid as a resolving agent. Compounds of the formula (III) containing two centres of asymmetry may be separated into their diastereoisomers by fractional crystallisation from a suitable solvent, for example from methanol or ethyl acetate. After such separation the individual components of the diastereoisomer may be obtained by resolution in known manner, for example using an optically active acid as a resolving agent.

Stereospecific synthesis may also be employed in order to obtain specific enantiomers. Thus, for example, a single enantiomer of a compound of the formula (V) may be used to react with a compound of the formula (VI) prior to borohydride or catalytic reduction. Similarly a single enantiomer of a compound of the formula (VIII) (where $A^1$ and $A^2$ are different) may be used to react with a compound of the formula (X) prior to borohydride reduction. The enantiomers produced by these processes may then be separated by conventional means such as fractional crystallisation from a suitable solvent, for example ethyl acetate.

Also a single enantiomer of formula (VII) may be reacted with a single enantiomer of formula (VIII) to give a specific enantiomer.

Suitable optically active acids for use in resolution processes are described in Topics In Stereochemistry, Vol. 6, Wiley Interscienece 1971, Allinger N. L. and Eliel W. L. eds.

The processes of European Application No. 79301197.4, Japanese Application No. 82545/79 and U.S. Application Ser. No. 051,440 are incorporated herein by cross reference.

The following Examples illustrate the invention.

EXAMPLE 1

N-(2-[4-Carbomethoxyphenyl]-1-methylethyl)-2-(3-chlorophenyl)-2-hydroxyethanamine 3-Chlorophenylglyoxal (1.6 g) and 2-(4-carbomethoxyphenyl)ethanamine (1.8 g) were heated in refluxing benzene (100 ml) under a Dean and Stark head until the theoretical amount of water had been collected. The solvent was replaced with methanol (100 ml) and sodium borohydride (2.5 g) was added portionwise with ice cooling. The mixture was stirred for 2 h, the solvent was evaporated and the residue was paritioned between water (100 ml) and chloroform (100 ml). The dried organic extract was evaporated and crystallised from methanol to give a single diastereoisomer m.p. 94°-96° (0.19 g) (less active diastereoisomer).

$^{13}$C n.m.r. (DMSO). 19.99 ppm. $\tau$(d$_6$DMSO) 9.05 (3H, t, J=6 Hz), 6.90-7.70 (7H, m), 6.15 (3H, s), 5.35 (1H, m), 2.50-2.80 (6H, m), 2.04 (2H, d, J=8 Hz). Recrystallisation from hexane of the residue from the mother liquor, gave a product m.p. 71°-81° (0.26 g) which was shown to contain 31% of the more active diastereoisomer.

$^{13}$C n.m.r. (DMSO) 19.78 ppm (31%), 19.99 (69%).

EXAMPLE 1A

1R, 2'S:1S, 2'R-N-(2-[4-Carbomethoxyphenyl]-1-methylethyl)-2'-(3-chlorophenyl)-2'-hydroxyethanamine 3-Chlorophenylglyoxal (1.6 g) and 2-(4-carbomethoxyphenyl)-1-methylethanamine (1.8 g) were heated in refluxing benzene (100 ml) under a Dean and Stark head until the theoretical amount of water had been collected. The solvent was replaced with methanol (100 ml) and sodium borohydride (2.5 g) was added portionwise with ice cooling. The mixture was stirred for 2 h, the solvent was evaporated and the residue was partitioned between water (100 ml) and chloroform (100 ml). The dried organic extract was evaporated and crystallised from methanol to give a single diastereoisomer of 1R, 2'S:1S, 2'R-N-(2-[4-carbomethoxyphenyl]-1-methylethyl)-2'-(3-chlorophenyl)-2'-hydroxyethanamine (95% diastereoisomeric purity by g.c.) m.p. 94°–96° (0.19 g) (less active diastereoisomer) $^{13}$C n.m.r. ($d_6$DMSO) 19.99 ppm.

$^1$H n.m.r. $\tau$($d_6$DMSO) 9.05 (3H, d, J=6 Hz, 6.90–7.70 (7H, m), 6.15 (3H, s) 5.35 (1H, m), 2.50–2.80 (6H, m), 2.04 (2H, d, J=8 Hz).

EXAMPLE 2

1R, 2'R:1S, 2'S-N-(2-[4-Carbomethoxyphenyl]-1-methylethyl)-2'-(3-chlorophenyl)-2'-hydroxyethanamine A mixture of 1-(4-carbomethoxyphenyl)propan-2-one (6.0 g) and 2-(3-chlorophenyl)-2-hydroxyethanamine (5.4 g) in benzene (100 ml) was refluxed under Dean and Stark conditions for 3 hours. The solvent was replaced with methanol (100 ml) and sodium borohydride (4.0 g) was added portionwise with ice cooling. The mixture was evaporated and the residue was partitioned between water (100 ml) and chloroform (100 ml). The organic phase was dried (magnesium sulphate) and evaporated to an oil which was crystallised from methanol to remove the high melting point diastereoisomer, (2.1 g). The residue (4.5 g) was chromatographed on silica gel 60 in 2% methanol/chloroform, to give an oil which was crystallised from methanol/ether to remove further high melting point diastereoisomer (1.8 g). The residue from the mother liquors was treated with the theoretical amount of fumaric acid in ethanol to give predominantly 1R, 2'R:1S, 2'S-N-(2-[4-carbomethoxyphenyl]-1-methylethyl)-2'-(3-chlorophenyl)-2'-hydroxyethanamine as the fumarate salt m.p. 156°–162° (76% diastereoisomer purity by g.c.)

Hnmr $\tau$(DMSO $d_6$): 8.95 (3H, d, J=6 Hz), 6.7–7.4 (5H, m), 6.2 (3H, s), 5.2 (1H, m), 3.5 (1H, s), 3.3 (2H, br), 2.7 (4H, s), 2.65 (2H, d, J=8 Hz), 2.1 (2H, d, J=8 Hz). $^{13}$C n.m.r. (DMSO $d_6$) (free base): 19.78 ppm (76%) 19.99 ppm (24%).

EXAMPLE 3

1S, 2'R-N-(2-[4-Carbomethoxyphenyl]-1-methylethyl)-2'-(3-chlorophenyl)-2'-hydroxyethanamine 1S, 2'R-N-(2-[4-carbomethoxyphenyl]-1-methylethyl)-2'-(3-chlorophenyl)-2'-hydroxyethanamine was prepared as colourless crystals m.p. 105°–6° (99% enantiomeric purity by g.c.) by the method of Example 1A, replacing 2-(4-carbomethoxyphenyl)-1-methylethanamine with 1-S-2-(4-carbomethoxyphenyl)-1-methylethanamine.

EXAMPLE 4

N-(3-[4-Carbomethoxyphenyl]-1-methylpropyl)-2-(3-chlorophenyl)-2-hydroxyethanamine The title compound was obtained by the method of Example 2, replacing 1-(4-carbomethoxyphenyl)propan-2-one with 4-(4-carbomethoxyphenyl)butan-2-one. The oil obtained after the sodium borohydride reduction was chromatographed on silica gel 60 in 2% methanol/chloroform and N-(3-[4-carbomethoxyphenyl]-1-methylpropyl)-2-(3-chlorophenyl)-2-hydroxyethanamine was obtained as the hydrochloride salt m.p. 143°–8° as a 52:48 mixture of diastereoisomers (by g.c.).

$^1$Hnmr $\tau$(CDCl$_3$) (free base): 8.9 (3H, d, J=6 Hz), 8.1–8.6 (2H, m), 7.0–7.6 (7H, m), 6.1 (3H, s), 5.4 (1H, m), 2.6–2.9 (6H, m), 2.1 (2H, d, J=8 Hz).

EXAMPLE 5

N-(2-[4-Carbomethoxyphenyl]-1, 1-dimethylethyl)-2-(3-chlorophenyl)-2hydroxyethanamine N-(2-[4-carbomethoxyphenyl]-1, 1-dimethylethyl)-2-(3-chlorophenyl)-2-hydroxyethanamine was obtained as the hydrochloride salt m.p. 78°–81° by the method of Example 1A, replacing 2-(4-carbomethoxyphenyl)-1-methylthanamine with 2-(4-carbomethoxyphenyl)-1, 1-dimethylethanamine.

$^1$Hnmr $\tau$(CDCl$_3$) (free base): 8.95 (6H, s), 6.8–7.3 (6H, m), 6.1 (3H, s), 5.3 (1H, m), 2.5–2.9 (6H, m), 2.1 (2H, d, J=8 Hz).

EXAMPLE 6

1R, 2'R-N-(2-[4-Carbomethoxyphenyl]-1-methylethyl)-2'-(3-chlorophenyl)-2'-hydroxyethanamine A solution of R-3-chlorostyrene oxide (2.3 g) in ethanol (10 ml) was added dropwise to a stirred, refluxing solution of 1R-2-(4-carbomethoxyphenyl)-1-methylethanamine (2.9 g) in ethanol (50 ml). Following complete addition the mixture was heated at reflux for 20 h, the solvent was evaporated and the residue was chromatographed on silica gel 60 in 2% methanol/chloroform. The title compound was obtained as an oil (2.4 g) and was converted to 1R, 2'R-N-(2-[4-carbomethoxyphenyl]-1-methylethyl)-2'-(3-chlorophenyl)-2'-hydroxyethanamine fumarate, m.p. 132–4[$\alpha$]$_D^{25}$ (ethanol) —36.2. (98% enantiomeric purity by g.c.).

$^1$Hnmr $\tau$(DMSO $d_6$): 8.9 (3H, d, J=6 Hz), 6.5–7.4 (5H, m), 6.1 (3H, s), 5.1 (1H, m), 3.4 (1H, s), 1.9–2.9 (8H, m).

EXAMPLE 7

1S, 2'R:1S, 2'S-N-3-[4-Carbomethoxyphenyl]-1-methylpropyl)-2'-(3-chlorophenyl)-2'-hydroxyethanamine The title compound was prepared by the method of Example 1A, replacing 2-(4-carbomethoxyphenyl)-1-methylethanamine with 1-S-3-(4-carbomethoxyphenyl)-1-methylpropanamine. Chromatography on the product on silica gel 60 in 2% methanol/chloroform and crystalisation from methanol gave 1S,2'R:1S, 2'S-N-3-[4-carbomethoxyphenyl]-1-methylpropyl)-2'-(3-chlorophenyl)-2'-hydroxyethanamine as a 50:50 mixture of enantiomers ($^{13}$C NMR). m.p. 62°–69°.

'Hnmr τ(CDCl₃): As Example 4.

EXAMPLE 8

N-(2-[4-Carboxamidophenyl]-1-methylethyl)-2-(3-chlorophenyl)-2-hydroxyethanamine N-(2-[4-carboxamidophenyl]-1-methylethyl)-2-(3-chlorophenyl)-2-hydroxyethanamine was prepared as a 20:80 mixture of diastereoisomers, m.p. 250°–254° from ethylacetate by the process of Example 2, replacing 1-(4-carbomethoxyphenyl) propan-2-one with 1-(4-carboxamidophenyl)propan-2-one.

τ(DMSO d₆): 9.1 (3H, d, J=6 Hz), 7.0–7.5 (5H, m), 5.35, (1H, m), 4.4–5.1 (2H, br), 2.5–2.9 (6H, m), 2.2 (2H, d, J=8 Hz).

EXAMPLE 9

N-(3-[4-Carbomethoxyphenyl]-1, 1-dimethylpropyl)-2-(3-chlorophenyl)-2-hydroxyethanamine N-(3-[4-carbomethoxyphenyl]-1, 1-dimethylpropyl)-2-(3-chlorophenyl)-2-hydroxyethanamine was prepared as colourless crystals m.p. 116.5°–117.5° C. from ether by the method of Example 1A, replacing 2-(4-carbomethoxyphenyl)-1-methylethanamine with 3-(4-carbomethoxyphenyl)-1, 1-dimethylpropanamine.

'Hnmr τ(CDCl₃): 8.83 (6H, s), 8.50–8.16 (2H, m), 8.16–6.93 (6H, m including two exchangeable protons), 6.07 (3H, s), 5.50–5.28 (1H, m), 2.96–2.56 (6H, m), 2.03 (2H, d, J=8 Hz).

EXAMPLE 10

N-(2-(4-carbomethoxyphenyl)ethyl)-2-(3-chlorophenyl)2-hydroxyethanamine

N-(2-(4-carbomethoxyphenyl)ethyl)-2-(3-chlorophenyl) 2-hydroxyethanamine was prepared and isolated as the hemihydrate, which was a colourless crystalline solid m.p. 112°–114° C. from benzene, by the method of Example 1A, replacing 2-(4-carbomethoxyphenyl)-1-methylethanamine with 2-(4-carbomethoxyphenyl)ethanamine.

'Hnmr τ(CDCl₃): 7.92–7.61 (3H exchangeable, br), 7.50–6.91 (6H, m), 6.06 (3H, s), 5.50–5.23 (1H, m), 2.94–2.55 (6H, m), 2.01 (2H, d, J=8 Hz).

EXAMPLE 11

N-(2-[4-N'-Methylcarboxamidophenyl]-1, 1-dimethylethyl)-2-(3-chlorophenyl)-2-hydroxyethanamine N-(2-[4-N'-Methylcarboxamidophenyl]-1, 1-dimethylethyl)-2-(3-chlorophenyl)-2-hydroxyethanamine was prepared as colourless crystals m.p. 136°–142° by the method of Example 1A, replacing 2-(4-carbomethoxyphenyl)-1-methylethanamine by 2-(4-N-methylcarboxamidophenyl)-1, 1-dimethylethanamine.

'Hnmr τ(d₆ DMSO): 9.06 (6H, s), 8.6 (1H, broad, disappears with D₂O), 7–7.7 (7H, m), 5.44 (1H, t, J=6 Hz), 4.64 (1H, broad, disappears with D₂O), 2.67 (6H, m), 2.27 (2H, d, J=8 Hz), 1.67 (1H, broad, q, disappears with D₂O).

EXAMPLE 12

N-(3[4-N'-Methylcarboxamidophenyl]-1, 1-dimethylpropyl)-2-(3chlorophenyl)-2-hydroxyethanamine The compound of Example 9, N-(3-[4-carbomethoxyphenyl]-1, 1-dimethylpropyl)-2-(3-chlorophenyl)-2-hydroxyethanamine (1.77 g) was dissolved in methanolic methylamine (20 ml) and heated in an autoclave at 100° for 5 h. The solution was allowed to cool, the solvent evaporated and the residual solid re-crystallised from ethylacetate to give N-(3-[4-N'-methylcarboxamidophenyl]-1, 1-dimethylpropyl)-2-(3-chlorophenyl)-2-hydroxyethanamine (0.92 g) m.p. 151–8.

'Hnmr τ(d₆ DMSO): 8.97 (6H, s), 8.31–8.67 (2H, m), 7.15–7.67 (9H, m), 6.4 (2H, broad), 5.44 (1H, t, J=6 Hz), 2.55–3.0 (6H, m), 2.28 (2H, d, J=8 Hz), 1.7 (1H, broad q).

EXAMPLE 13

N-(3-[4-Carboxamidophenyl]-1, 1-dimethylpropyl)-2-(3-chlorophenyl)-2-hydroxyethanamine N-(3-[4-Carboxamidophenyl]-1, 1-dimethylpropyl)-2-(3-chlorophenyl)-2-hydroxyethanamine was prepared as a crystalline solid m.p. 128–132 (ethylacetate) as described in Example 1A, replacing 2-(4-carbomethoxyphenyl)-1-methylethanamine with 3-(4-carboxamidophenyl)-1, 1-dimethylpropanamine.

τ(d₆ DMSO): 8.67 (6H, s), 8.27–8.7 (2H, m), 7.3–7.7 (4H, m), 5.41 (1H, t, J=6 Hz), 3.0–2.5 (6H, m), 2.25 (2H, d, J=8 Hz).

EXAMPLE 14

N-(3-[4-Carbomethoxyphenyl]propyl)-2-(3-chlorophenyl)-2-hydroxyethanamine

N-(3-[4-Carbomethoxyphenyl]propyl)-2-(3-chlorophenyl)-2-hydroxyethanamine was prepared as a crystalline solid, m.p. 89°–92° (hexane) by the method of Example 1A, replacing 2-(4-carbomethoxyphenyl)-1-methylethanamine by 3-(4-carbomethoxyphenyl)-propanamine.

'Hnmr τ(CDCl₃): 8.15 (2H, m), 7.0–7.8 (9H, m), 6.13 (3H, s), 5.35 (1H, dd), 2.75 (6H, m), 2.1 (2H, d, J=8 Hz).

EXAMPLE 15

N-(3-[4-N'-Methylcarboxamidophenyl]propyl)-2-(3-chlorophenyl)-2-hydroxyethanamine N-(3-[4-N'-Methylcarboxamidophenyl]propyl)-2-(3-chlorophenyl)-2-hydroxyethanamine was prepared as a crystalline solid, m.p. 116°–118° (ethylacetate) by the method of Example 12, replacing N-(3-[4-carbomethoxyphenyl]-1, 1-dimethylpropyl)-2-(3-chlorophenyl)-2-hydroxyethanamine by N-(3-[4-carbomethoxyphenyl]propyl)-2-(3-chlorophenyl)-2-hydroxyethanamine (the compound of Example 14).

'Hnmr τ(CDCl₃/DMSO): 8.15 (2H, m), 7.35 (6H, m), 7.15 (3H, d, J=4 Hz, collapses to singlet on D₂O), 6.05 (2H, broad, disappears on D₂O), 5.3 (1H, broad t), 2.75 (6H, m), 2.2 (2H, d, J=8 Hz), 1.95 (1H, q, disappears on D₂O).

PREPARATION 1

1-S-2-(4-Carbomethoxyphenyl)-1-methylethanamine

A mixture of 1-(4-carbomethoxyphenyl)propan-2-one (15.3 g) and (−)-α-methylbenzylamine (9.65 g) was stirred in refluxing benzene (150 ml) under a Dean and Stark apparatus until the theoretical amount of water had been collected. The solvent was evaporated and replaced with ethanol (200 ml). Raney Nickel (from 20 ml of suspension in water, washed several times with ethanol) was added and the mixture was hydrogenated in a Parr hydrogenator at ambient temperature under a hydrogen pressure of 60 psi. for 36 h. The catalyst was filtered off and the solvent was evaporated. The residue was taken up in either (50 ml) and treated with ethereal hydrogen chloride (50 ml). The solid was collected and dried (22.75 g) m.p. 216°–220°. Recrystallisation from methanol/acetonitrile gave N-(1'-S-1'-phenylethyl)-1-S-2-(4-carbomethoxyphenyl)-1-methylethanamine hydrochloride as a colourless solid (13.5 g). m.p. 227°–228°.

$^{13}$C nmr ppm (DMSO d$_6$): 15.93, 19.75, 37.34, 51.86, 52.18, 54.43, 127.80, 128.08, 128.71, 128.80, 129.24, 137.44, 142.58, 165.83.

The solid prepared above was dissolved in methanol (200 ml), 5% Pd/C (500 mg) was added and the mixture was shaken in the Parr under a hydrogen pressure of 60 psi at 60° for 8 h. The catalyst was removed, the solvent was evaporated and the residue was recrystallised from acetonitrile to give 1-S-2-(4-carbomethoxyphenyl)-1-methylethanamine hydrochloride as colourless needles (7.1 g), m.p. 208°–211°[α]$_D^{25}$ (water) = +19.9°.

'Hnmr τ(DMSO d$_6$): 8.78 (3H, d, J=6 Hz), 6.0–7.5 (3H, m), 6.08 (3H, s), 2.53 (2H, d, J=9 Hz), 1.98 (2H, d, J=9 Hz, 1.36 (3H, br).

PREPARATION 2

1-R-2-(4-Carbomethoxyphenyl)-1-methylethanamine

N-(1'-R-1'-phenylethyl)-1-R-2-(4-carbomethoxyphenyl)-1-methylethanamine hydrochloride was prepared by the method outlined in Preparation 1, replacing (−)-α-methylbenzylamine with (+)-α-methylbenzylamine. Re-crystallisation from ethylacetate/acetonitrile gave a colourless solid, m.p. 221°–223°. $^{13}$C nmr as Preparation 1.

Debenzylation was achieved as described in Preparation 1 and the title compound (hydrochloride) was obtained as a colourless solid, mp 207°–211° from methanol/acetonitrile. [α]$_D^{25}$ (water) = −18.9°. 'Hnmr as Preparation 1.

PREPARATION 3

1-S-3-(4-Carbomethoxyphenyl)-1-methylpropanamine

N-(1'-S-1'-phenylethyl)-1-S-3-(4-carbomethoxyphenyl)-1-methylpropanamine hydrochloride was prepared by the method outlined in Preparation 1, replacing 1-(4-carbomethoxyphenyl)propan-2-one with 4-(4-carbomethoxyphenyl)butan-2-one. Recrystallisation several times from acetonitrile gave a colourless solid, mp 203°–205°.

Debenzylation was achieved as described in Preparation 1 and the title compound (hydrochloride) was obtained as colourless crystals from methanol/acetonitrile mp 168°–172°. [α]$_D^{25}$ (methanol = −7.2°.

PREPARATION 4

R-3-Chloromandelic Acid

A mixture of rac -3-chloromandelic acid (37.3 g) and (+)-ephedrine (32.4 g) in ethanol (200 ml) was warmed until completely dissolved. The solution was filtered, cooled and seeded. The crystalline precipitate was collected (30.6 g) m.p. 137.5°–145° and was twice recrystallised from ethanol to give colourless crystals (18.6 g) mp 147°–150°. The crystals were treated with 2 M hydrochloric acid (50 ml) and the mixture was extracted with chloroform (3×100 ml). The dried (MgSO$_4$) extracts were evaporated and the residue was crystallised from benzene to give the title compound (8.2 g) m.p. 102°–103° [α]$_D^{25}$ (Acetone) = −117.5°.

PREPARATION 5

R-3-Chlorostyrene oxide

Borane: methyl sulphide complex (18 ml) was added dropwise to a stirred solution of R-3-chloromandelic acid (8.7 g) in dry tetrahydrofuran (50 ml) under nitrogen. After the addition of the first few drops of the borane: methyl sulphide complex the mixture was warmed under reflux for the rest of the addition. The mixture was heated under reflux for 2 h then cooled in ice and methanol (50 ml) was added dropwise to destroy excess reagent. The solvent was evaporated, the residue was taken up in chloroform and dried (magnesium sulphate). Evaporation of the solvent gave crude R-2-(3-chlorophenyl)-2-hydroxyethanol (8.5 g) which was used without further purification.

A solution of 4-toluenesulphonyl chloride (9.1 g) in toluene (50 ml) was added dropwise to a stirred solution of R-2-(3-chlorophenyl)-2-hydroxyethanol (8.5 g) in pyridine (5.0 ml) and toluene (40 ml) with ice cooling. The reaction mixture stood at 0° for 48 h, filtered to remove precipitated pyridinium hydrochloride and the solvent was evaporated. The residue was dissolved in chloroform, washed with 2 M hydrochloric acid, with water and dried (magnesium sulphate). The solvent was evaporated to give crude R-2-(3-chlorophenyl)-2-hydroxy-1-(4-toluenesulphonyloxy)ethane (13.0 g) as an oil. This product was dissolved in dimethylsulphoxide (30 ml) containing water (12.5 ml) and sodium hydroxide (2.5 g) and allowed to stand at 0° for 16 h before pouring into ice/water. The product was extracted into 50% hexane/chloroform, dried and evaporated. Distillation of the residue gave the title compound as a colourless oil b.p. 68°–70°/0.1 mm (3.5 g) [α]$_D$≃(Ethanol = +10.8°.

'Hnmrτ(CDCl$_3$): 7.3 (1H, m), 6.9 (1H, m), 6.35 (1H, m), 2.65–2.9 (4H, m).

PREPARATION 6

3-(4-Carbomethoxyphenyl)-1, 1-dimethylpropanamine

Thionyl chloride (31 ml) was added dropwise to methanol (210 ml) at −70°. The solution was stirred for 10 mins and then 3-(4-carboxyphenyl)-1, 1-dimethylpropanamine hydrochloride (20 g) in methanol was added dropwise. The reaction mixture was allowed to warm to ambient temperature and then heated under reflux for 1 h. The solvent was evaporated, the residue partitioned between potassium carbonate and ether and the organic layer dried. Removal of the solvent gave the title compound, as an oil.

'Hnmr τ(CDCl$_3$): 8.8 (6H, s), 8.7 (2H, s), 8.35 (2H, m), 7.5–7.0 (2H, m), 6.1 (3H, s), 2.75 (2H, d, J=8 Hz), 2.05 (2H, d, J=8 Hz).

DEMONSTRATION OF EFFECTIVENESS OF COMPOUNDS (i) Anti-obesity activity

The compounds were administered by oral gavage in water or carboxymethyl-cellulose suspension to genetically obese mice daily for 28 days. At the end of the time the carcass composition was determined. The results obtained were as follows:

| COMPOUND OF EXAMPLE | DOSE mg/kg p.o. | g-LIPID PER MOUSE | |
|---|---|---|---|
| | | TREATED | CONTROL |
| 1A | 13.3 | 12.1 | 18.2 |

| COMPOUND OF EXAMPLE | DOSE mg/kg p.o. | g-LIPID PER MOUSE | |
|---|---|---|---|
| | | TREATED | CONTROL |
| 2 | 1.1 | 14.2 | 18.2 |
| 5 | 11.0 | 16.6 | 20.0 |

(ii) Effect on energy expenditure

The effect of the compounds on the energy expenditure of mice was demonstrated by means of the following procedure.

Female CFLP mice each weighing approximately 24 g, were given food and water ad lib before and during the experiment. The compounds were dissolved in water by addition of the same number of moles hydrochloric acid, and these solutions were administered orally to each of 12 mice. A further 12 mice were dosed orally with water. The mice were placed in boxes through which air was drawn and the oxygen content of the air leaving the boxes was measured. The energy expenditure of the mice was calculated for 21 h after dosing from the volume of air leaving the boxes and its oxygen content following the principles described by J B de V Weir (J. Physiol. (London) (1949) 109, 1–9). The food intake of the mice was measured over this same period of 21 h. The results are expressed as a percentage of the mean food intake or rate of energy expenditure of the mice dosed with water.

| COMPOUND OF EXAMPLE | DOSE mg/kg p.o. | PERCENTAGE OF CONTROL VALUES | |
|---|---|---|---|
| | | ENERGY EXPENDITURE | FOOD INTAKE |
| 1A | 11.3 | 120 | 93 |
| 2 | 3 | 125 | 91 |
| 3 | 9.7 | 104 | 73 |
| 4 | 22 | 111 | 101 |
| 5 | 22 | 117 | 81 |
| 6 | 5.6 | 135 | 99 |
| 7 | 20.1 | 107 | 95 |
| 8 | 18.5 | 115 | 86 |
| 9 | 20.9 | 101 | 78 |
| 10 | 19.1 | 123 | 90 |
| 11 | 20.1 | 110 | 102 |
| 12 | 20.9 | 117 | 96 |
| 13 | 20.1 | 112 | 109 |
| 14 | 19.4 | 119 | 111 |
| 15 | 19.3 | 119 | 90 |

(iii) Cardiac activity

Rat hearts were perfused by the Langendorff procedure. Hearts were dissected free within 30 seconds of death and reverse perfused via the aorta and coronary vessels with Krebs-Ringer bicarbonate solution (pH 7.4, 37° C.) gassed with 95% $O_2$:5% $CO_2$. The flow rate was between 8–12 mls/min. Responses were obtained after injection of drug dissolved in isotonic saline into the perfusion media. Heart rate and tension were displayed on an Ormed MX2P recorder via a tension transducer and heart ratemeter.

Results are expressed as a percentage of the response due to salbutamol.

| COMPOUND OF EXAMPLE | DOSE ADDED (µg) | HEART TENSION | HEART RATE |
|---|---|---|---|
| 1A | 30 | 33 | 40 |
| 2 | 30 | 52 | 144 |
| 3 | 10 | 33 | 86 |
| 4 | 10 | 13 | 38 |
| 5 | 30 | 15 | 33 |
| 6 | 10 | 50 | 88 |
| 8 | 30 | 65 | 100 |
| 10 | 30 | 52 | 43 |
| 13 | 10 | 15 | 31 |

(iv) Hypoglycaemic activity

Female CFLP mice, weighing approximately 25 g, were fasted for 24 hours prior to the study. The compounds under study were administered orally to each of 8 mice. 30 minutes later a blood sample (20 ml) was obtained from the tail for the analysis of blood glucose. Immediately after taking this blood sample, each mouse was given glucose (1 g/kg body weight sub-cutaneously). Blood samples were then obtained from each mouse at 30 minute intervals for 120 minutes.

Compounds that produced a significant (P 0.05) reduction of blood glucose, compared with control mice given water, at any time interval were considered active. The area under the blood glucose curve over the 2 hour period after giving the glucose load was calculated for each compound and compared with the value for control animals.

| COMPOUND OF EXAMPLE | DOSE mg/kg p.o. | REDUCTION IN AREA UNDER BLOOD GLUCOSE CURVE % |
|---|---|---|
| 1A | 1 | 27 |
| 2 | 1 | 46 |
| 3 | 20 | 57 |
| 4 | 20 | 47 |
| 5 | 20 | 45 |
| 6 | 1 | 56 |
| 7 | 20 | 31 |
| 8 | 1 | 15 |
| 9 | 20 | 11 |
| 11 | 20 | 26 |
| 12 | 20 | 55 |
| 13 | 20 | 49 |
| 15 | 20 | 55 |

We claim:

1. A compound of formula (III)

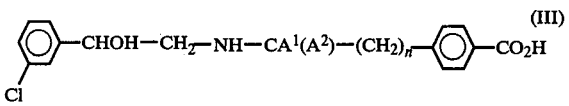

and esters, amides and pharmaceutically acceptable salts thereof, wherein
$A^1$ is hydrogen or methyl;
$A^2$ is hydrogen or methyl; and
n is 1, 2 or 3.

2. A compound according to claim 1 wherein $A^1$ is methyl, $A^2$ is hydrogen and n is 1, or wherein $A^1$ and $A^2$ are both hydrogen and n is 1 or 2.

3. The methyl ester, N'-substituted or N'-monomethyl substituted amide of a compound according to claim 1 or a pharmaceutically acceptable salt thereof.

4. A pharmaceutical composition having anti-obesity activity comprising a pharmaceutically effective amount of a compound according to claim 1 in association with a pharmaceutically acceptable carrier therefor.

5. A composition according to claim 4 in unit-dose form containing 0.1 to 500 mg per dosage unit.

6. A method for treating obesity in humans and domestic manuals which comprises administering an effective, non-toxic amount of a pharmaceutical composition according to claim 4.

7. A method according to claim 6 wherein there is administered a daily dose of from 0.1 to 500 mg to a human.

8. A method according to claim 6 wherein there is administered a daily dose of from 0.05 to 25 mg/kg to a domestic mammal.

9. A compound according to claim 1 selected from
N-(2-[4-Carbomethoxyphenyl]-1-methylethyl)-2-(3-chlorophenyl)-2-hydroxyethanamine
IR, 2'S:1S, 2'R-N-(2-[4-Carbomethoxyphenyl]-1-methylethyl)-2'-(3-chlorophenyl)-2'-hydroxyethanamine
IR, 2'R:1S, 2'-S-N-(2-[4-Carbomethoxyphenyl]-1-methylethyl)-2'-(3-chlorophenyl)-2'-hydroxyethanamine
1S, 2'R-N-(2-[4-Carbomethoxyphenyl]-1-methylethyl)-2'-(3-chlorophenyl)-2'-hydroxyethanamine
N-(3-[4-Carbomethoxyphenyl]-1-methylpropyl)-2-(3-chlorophenyl-2-hydroxyethanamine
N-(2-[4-Carbomethoxyphenyl]-1, 1-dimethyl-ethyl)-2-(3-chlorophenyl)-2-hydroxyethanamine
1R, 2'R-N-(2-[4-Carbomethoxyphenyl]-1-methylethyl)-2'-(3-chlorophenyl)-2'-hydroxyethanamine
1S,2'R:1S, 2'S-N-3-[4-Carbomethoxyphenyl]-1-methylpropyl)-2'-(3-chlorophenyl)2'-hydroxyethanamine
N-(2-[4-Carboxamidophenyl]-1-methylethyl)-2-(3-chlorophenyl)-2-hydroxyethanamine
N-(3-[4-Carbomethoxyphenyl]-1, 1-dimethylpropyl)-2-(3-chlorophenyl)-2-hydroxyethanamine
N-(2-(4-Carbomethoxyphenyl)ethyl)-2-(3-chlorophenyl)2-hydroxyethanamine
N-(2-[4-N'-Methylcarboxamidophenyl]-1, 1-dimethylethyl)-2-(3-chlorophenyl)-2-hydroxyethanamine
N-(3[4-N'-Methylcarboxamidophenyl]-1, 1-dimethylpropyl)-2-(3-chlorophenyl)-2-hydroxyethanamine
N-(3-[4-Carboxamidophenyl]-1, 1-dimethylpropyl)-2-(3-chlorophenyl)-2-hydroxyethanamine
N-(3-[4-Carbomethoxyphenyl]propyl)-2-(3-chlorophenyl)-2-hydroxyethanamine
N-(3-[4-N'-Methylcarboxamidophenyl]propyl)-2-(3-chlorophenyl)-2-hydroxyethanamine.

10. The compound of claim 1 which is 1R,2'R-N-(2-[4-Carbomethoxyphenyl]-1-methylethyl)-2'-(3-chlorophenyl)-2'-hydroxyethanamine.

* * * * *